United States Patent [19]
Hacker et al.

[11] Patent Number: 5,617,250
[45] Date of Patent: Apr. 1, 1997

[54] RADIATION PROJECTION ARRANGEMENT WITH INTEGRATED RADIATION INDICATOR

[75] Inventors: Erik Hacker; Hubert Pohlack, both of Jena, Germany

[73] Assignee: Jenoptik GmbH, Jena, Germany

[21] Appl. No.: 196,077

[22] PCT Filed: Jun. 28, 1993

[86] PCT No.: PCT/EP93/01647

§ 371 Date: Feb. 15, 1994

§ 102(e) Date: Feb. 15, 1994

[87] PCT Pub. No.: WO94/01793

PCT Pub. Date: Jan. 20, 1994

[30] Foreign Application Priority Data

Jul. 1, 1992 [DE] Germany .......................... 42 21 523.4

[51] Int. Cl.$^6$ ....................................................... G02B 1/10
[52] U.S. Cl. .......................... 359/582; 359/584; 359/585; 359/590; 359/885; 359/887; 250/474.1; 250/482.1
[58] Field of Search ...................... 359/585, 590, 359/582, 584, 885, 887, 889, 900; 351/44; 2/432; 250/474.1, 482.1, 487.1, 488.1

[56] References Cited

U.S. PATENT DOCUMENTS

| | | | |
|---|---|---|---|
| 3,499,697 | 3/1970 | Edwards | 359/590 |
| 3,519,339 | 7/1970 | Hutchinson et al. | 359/890 |
| 3,838,282 | 9/1974 | Harris | 250/487.1 |
| 3,899,677 | 8/1977 | Hori et al. | 250/487.1 |
| 4,567,122 | 1/1986 | Baldry et al. | 2/432 |
| 4,626,445 | 12/1986 | Dobrowolski et al. | 427/7 |
| 4,783,379 | 11/1988 | Wickersham et al. | 428/607 |
| 4,865,405 | 9/1989 | Kageyama | 359/890 |
| 4,925,259 | 5/1990 | Emmett | 359/589 |
| 4,926,045 | 5/1990 | Hosoi et al. | 250/585 |
| 4,931,642 | 6/1990 | Hosoi et al. | 250/586 |
| 4,944,026 | 7/1990 | Arakawa et al. | 250/488.1 |
| 4,994,352 | 2/1991 | Strandjord et al. | 430/495 |
| 5,023,944 | 6/1991 | Bradley | 455/611 |
| 5,084,623 | 1/1992 | Lewis et al. | 250/474.1 |

(List continued on next page.)

FOREIGN PATENT DOCUMENTS

| | | | |
|---|---|---|---|
| 188117 | 12/1956 | Austria . | |
| 268722 | 2/1969 | Austria . | |
| 0080182 | 6/1983 | European Pat. Off. | G02B 5/28 |
| 2479482 | 10/1981 | France | G02B 5/28 |
| 2-28616 | 1/1990 | Japan | G02C 7/16 |
| 2215075 | 9/1989 | United Kingdom | 359/890 |
| 9309449 | 5/1993 | WIPO | G02B 5/28 |

OTHER PUBLICATIONS

H. K. Pulker, "Laser Protection Filters for λ=633, 694 and 1060 nm", *Thin Solid Films*, 13, No. 2, 15 Nov. 1972, pp. 291–298.

N.A. Borisevich et al., "Infrared Filters," NASA Report No. TT F–814 Aug. 1974 pp. 206–208.

R.N. Singh et al, "Antilaser Filter for CW 6328Å He–Ne Laser", Indian Journal of Pure & Applied Physics, vol. 13, Apr. 1975, pp. 254–257.

Pohlack et al, "Induced Resonance Absorption in Thin Films" SPIE v.1782 Thin Films for Optical Systems (1992) p122.

Hacker et al, "Structure–Properties Relationships in Optical Coatings" Physica Scripta v.T49 (1993) p525.

*Primary Examiner*—Paul M. Dzierzynski
*Assistant Examiner*—John Juba, Jr.
*Attorney, Agent, or Firm*—McAulay Fisher Nissen Goldberg & Kiel, LLP

[57] ABSTRACT

An arrangement is produced for protection against harmful effects of radiation and for indicating such radiation which can preferably be designed as a viewing window or as goggles and can be used for protecting the eyes from injury due to high-intensity electromagnetic radiation. It includes a transparent substrate and a sequence of thin optical layers which are applied to this substrate and are arranged according to the principle of an optical thin-film resonance absorber system.

16 Claims, 3 Drawing Sheets

U.S. PATENT DOCUMENTS

| | | | |
|---|---|---|---|
| 5,173,811 | 12/1992 | Gumbs | 359/885 |
| 5,206,118 | 4/1993 | Sidney et al. | 250/474.1 |
| 5,214,530 | 5/1993 | Coombs et al. | 359/585 |
| 5,249,175 | 9/1993 | Akahira et al. | 369/275.1 |
| 5,434,663 | 7/1995 | Maule | 356/300 |
| 5,493,442 | 2/1996 | Buchholz et al. | 359/885 |
| 5,519,522 | 5/1996 | Fergason | 359/590 |

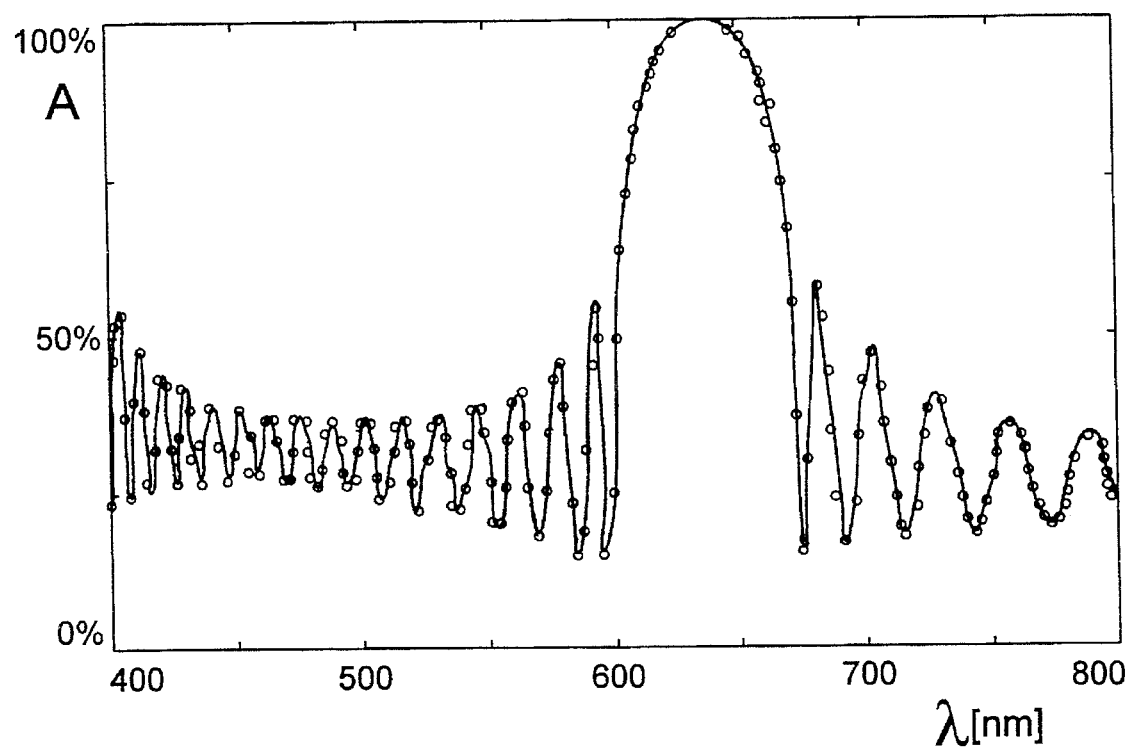
F I G. 5
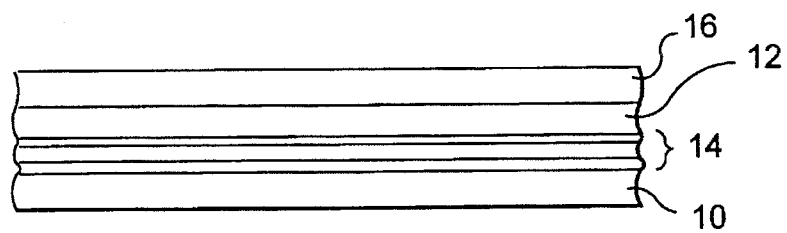
F I G. 6

RADIATION PROJECTION ARRANGEMENT WITH INTEGRATED RADIATION INDICATOR

BACKGROUND OF THE INVENTION a) Field of the Invention

The invention is directed to an arrangement for protection against harmful effects of radiation and for indicating such radiation which can preferably be designed as a viewing window or as goggles and can be used for protecting the eyes from injury due to high-intensity electromagnetic radiation.

b) Background Art

Radiation protection devices, particularly for protecting the eyes from high-energy monochromatic radiation of high surface or areal density, e.g. laser radiation, are known in numerous embodiment forms. They are mostly constructed as plates or foils of transparent material and provided with flashed materials which have a spectral filtering effect which extensively prevents the penetration of the spectral range of radiation from which the eyes are to be protected, but which admits the harmless spectral range to an extent enabling observation of the events within the space endangered by radiation, particularly in the immediate vicinity of the source of radiation.

Such flashed materials on transparent carriers are often constructed as sequences of thin interference coatings or layers of material whose properties and thickness are selected in a known manner in such a way that the interference layer system has a high reflection factor (near 100%) in the spectral range of hazardous radiation, but is only relatively slightly reflective in the neighboring spectral ranges.

Construction principles of light filtering by means of the cooperation of the spectral functions of interference filters (e.g. Fabry-Perot type or multi-cavity narrow-band filters) and absorption filters are known, for example, from "Infrared Filters" by A. Borisevich, V. G. Vereshehagain, and M. A. Validov, 1971, pages 206–208. The construction principles described in this literature cause a blocking of the transmission ranges of a higher order occurring as a result of the periodicity in interference filters by means of a combination of interference filters and absorbent substrates and/or superstrata (e.g. cemented groups) having a short-pass and/or long-pass filter characteristic. The light-blocking function can be improved when supplementing this combination by additional, usually absorbent interference layer filters as blocking groups (short-passes, long-passes). For example, the Ge/ZnS long-pass blocking filters which are frequently used in the infrared range block the entire visible spectrum by means of the absorption of germanium.

Fabry-Perot type metallic-film or metal-dielectric interference filters in which the narrow-band transmission characteristic is produced by embedding a dielectric spacing layer on both sides of semi-transparent metal mirrors is known from H. A. M. Macleod, "Thin-Film Optical Filters", Adam Hilger Ltd., Bristol (1986), pages 292–308.

Further, layer systems having absorbent and nonabsorbent layers with induced transmission in which the set of problems relating to absorption are mitigated by suitably influencing the field strengths of the stationary electrical field in the locations of the absorbent layers are known from B. V. Landan, P. H. Lissberger, "Theory of Induced Transmission Filters in Terms of Concept of Equivalent Layers", JOSA 62 (1972), No. 11, pages 1258–1264.

The described layer systems for radiation protection arrangements safely protect the eyes of the operator working in the area of the radiation field or the eyes of other persons present in the immediate vicinity from harmful radiation. On the other hand, such known arrangements have severe disadvantages insofar as the user of such a protective arrangement cannot ascertain whether or not or at what time he is exposed to the threat of radiation and after leaving the hazardous radiation zone it is no longer possible to verify any exposure to radiation which might have occurred so that the causes of exposure can also not be eliminated.

SUMMARY OF THE INVENTION

The invention has a primary object of providing a radiation protection arrangement with an automatic indicator which effectively protects against hazardous radiation of a wavelength $\lambda_0$ and in which a selective or localized change in portions of the material of the protective arrangement which can be verified visually, in particular by transparency or reflection, is produced in the event of hazardous radiation. In so doing, the protective action of the radiation protection arrangement is not impaired at any time before, during or after an irreversible or reversible change.

This object and other objects are is met by an arrangement according to the invention.

The arrangement according to the invention includes a transparent carrier plate, disk or foil and a sequence of thin optical layers which are applied to such a carrier, the material and thickness of the layers being selected and arranged so as to ensure a high level of protection against the transmission of the hazardous spectral interval with sufficient transparency in the rest of the visible spectral range and exposure to radiation can be monitored with the same arrangement.

The isolation of hazardous radiation of wavelength $\lambda_0$ and the prevention of its transmission are effected first by selective absorption within a layer of the protective layer system, rather than by reflection corresponding to the known thin-film radiation protection arrangement. Depending on the physical and chemical properties of the layer substance, the transformation of radiation energy into thermal energy produces different structural and/or chemical changes in the absorbent layer of the arrangement according to the invention at increased temperature, for example, localized destruction of the layer (ablation), material distortion, bubble formation, changes in texture, discoloration, oxidation or other phase and modification changes which serve, according to a principle idea of the invention, as visible irregularities in the material to indicate exposure of the protective arrangement to radiation. These irregularities in the material may be irreversible or reversible. If at least one of the aforementioned degradation processes results in the elimination of selective absorption in the absorbent layer of the layer system, the substrate layer system located behind it ensures that the radiation protection is maintained, preferably by reflection or by a combined reflecting and absorbing action.

The indication or conversion sensitivity of a thin absorbent layer for producing visible changes in material based on the effects of photothermal or photochemical transformation of energy is defined in a known manner as:

$$R_c = const \cdot (1/Q_{rad,\ min}),$$

where $Q_{rad,\ min}$ is the occurring radiation energy at wavelength $\lambda_0$ which is a minimum requirement for initiating the transformation effect. At a constant beam cross section, the threshold value $Q_{rad, min}$ decreases and the indication sensitivity accordingly increases, the lower the density $\rho$ and the specific heat c of the absorbent layer material and the lower the increase in temperature required for the change in material (for example, up to the melting point) and the greater the absorption density A/d, where A designates the proportion of radiation energy striking the protective arrangement at wavelength $\lambda_0$ and absorbed in the layer of thickness d.

The relevant quantity A/d for the indication sensitivity is decisively increased in the arrangement according to the invention compared to conventional optical absorption processes in that the entire sequence of layers is formed as an optical resonance absorber system according to POHLACK (DD-WP 146 224, DD-WP 152 638) in which the absorbent layer assumes the function of the absorbent resonator for the wavelength $\lambda_0$ of the hazardous radiation. As is known, such a layer system—in contrast to the exponentially decaying absorption in expanded absorbers of the same material which are not capable of resonance—produces 100-percent or virtually 100-percent absorption already within extremely thin layers, and thus achieves extremely high absorption densities A/d in the spectral range around the wavelength $\lambda_0$ and accordingly contributes to the desired decrease in the energy threshold for triggering significant photothermal (or photochemical) transformation effects.

In order to keep down costs for the radiation protection and indication of radiation in terms of film technique, the material to be selected for the absorbent resonant layer should have, according to the invention, an absorption coefficient k greater than 0.01 and preferably greater than 1 in the spectral range containing the wavelength $\lambda_0$ of the hazardous radiation.

Moreover, as is evident from the preceding remarks concerning the photochemical transformation process, in order to achieve an indication of radiation which is as sensitive as possible it is advisable that the selected absorbent materials suitable for the desired photothermal effect should be those having a relatively low specific heat and a relatively low mass density.

According to the invention, the portion of the overall system that represents the rear resonator wall and is arranged behind the resonant layer in the radiating direction is formed as a combination of interference layers which have different refractive indices and are only very slightly absorbent, if at all, which combination has a high reflection factor at least in the spectral range of the hazardous radiation and a sequence of low and high or high and low layer refractive indices alternating in the radiating direction. In order to achieve a high resonator quality, the partial layer system arranged downstream of the resonator layer has a reflection factor relative to air greater than 99% at wavelength $\lambda_0$. This high reflection at a wavelength $\lambda_0$ serves at the same time to protect against radiation when the absorbent layer has become transparent or partially transparent to radiation due to the photothermal transformation process. In order to achieve a sufficient transparency of the protective arrangement, that is, sufficient transparency to light at least in parts of the visible spectrum, the reflection factor of the layer combination arranged behind the absorbent resonator layer should be less than 50% in the visible spectral range excluding the spectral interval containing the wavelength $\lambda_0$.

According to the invention, the portion of the overall layer system which represents the front resonator wall and is arranged in front of the resonant layer as viewed in the radiating direction is formed as a layer or combination of layers which eliminates reflection and effects a non-reflecting adaptation to the superstratum, e.g. air. If an optimal adaptation to the superstratum by means of interference layers is unnecessary, as for example when the superstratum already fulfills the optical function of the front resonator wall or when the resonance condition has already been met to a sufficient degree, although not completely, the arrangement according to the invention provides for direct contact between the resonant layer and the superstratum or for the interposition of a layer for mechanical protection and/or protection against corrosion which is optically ineffective at a wavelength $\lambda_0$; such a layer with the refractive index $n_s$ has a geometrical thickness of $$d_s = m \cdot \lambda_0 / (2 \cdot n_s),$$

where m is a positive whole number.

The features indicated above distinguish the layer arrangement according to the invention from arrangements of material which, while also utilizing photothermal transformation processes produced in absorbent materials by laser radiation for the purpose of optical data recording, nevertheless provide fundamentally different layer sequences which do not satisfy the conditions for optical layer resonance or which, in the case of arrangements analogous to resonance absorption, use rear resonator walls produced from metal or from metal and thin intermediate layers resulting in the known considerable thermal losses. Thus, none of these arrangements offers the preconditions for the high indication sensitivity of photothermal transformation. Such arrangements are not transparent because of the metallic layer and are therefore fundamentally unsuitable for application in an arrangement for protecting against radiation which is transparent in the visible spectral range.

In cases where, in spite of the suggested increase in the photothermal transformation effectiveness by means of increasing the absorption density A/d, the threshold values for triggering a photothermal (or photochemical) effect within the absorbent layer are not yet achieved due to low radiation intensities, the indication sensitivity is additionally increased, according to another basic idea of the invention, by means of modifying the arrangement and verification of such a low-energy radiation is made possible in this way.

For this purpose, an arrangement according to the invention contains an additional layer of a material which already exhibits clear changes, e.g. localized melting, sublimation, evaporation, discoloration or other temperature-dependent phenomena, at temperatures not yet sufficient to bring about visible photothermal transformation effects in the absorbent layer. This additional layer, which is preferably arranged in direct contact with the absorption layer, can be nonabsorbent in the spectral range with the hazardous radiation of wavelength $\lambda_0$ so that the processes occurring in this additional layer as a result of an increase in temperature are preferably brought about by thermal contact with the absorption layer, i.e. by heat conduction, rather than by photothermal transformation. An arrangement according to the invention also includes such additional layers having absorbent spectral ranges outside a spectral interval containing the wavelength $\lambda_0$ which are produced e.g. by dyeing in the additional layer material (e.g. as dye-in polymers). Within the scope of the inventive idea, such a step proves advisable, for example, when the wavelength $\lambda_0$ lies outside the visible spectrum and a clear indication of exposure to radiation in the visible spectrum is to be achieved.

For a better understanding of the present invention, reference is made to the following description and accompa-

BRIEF DESCRIPTION OF THE DRAWINGS

FIG. 5 shows the spectral curve of the absorption factor A of a thin-film resonance absorber system according to the first embodiment example.

FIG. 6 is a schematic side elevational view of an arrangement for protection against electromagnetic radiation of at least one wavelength, in accordance with the present invention.

DESCRIPTION OF THE PREFERRED EMBODIMENTS

Figure 1:
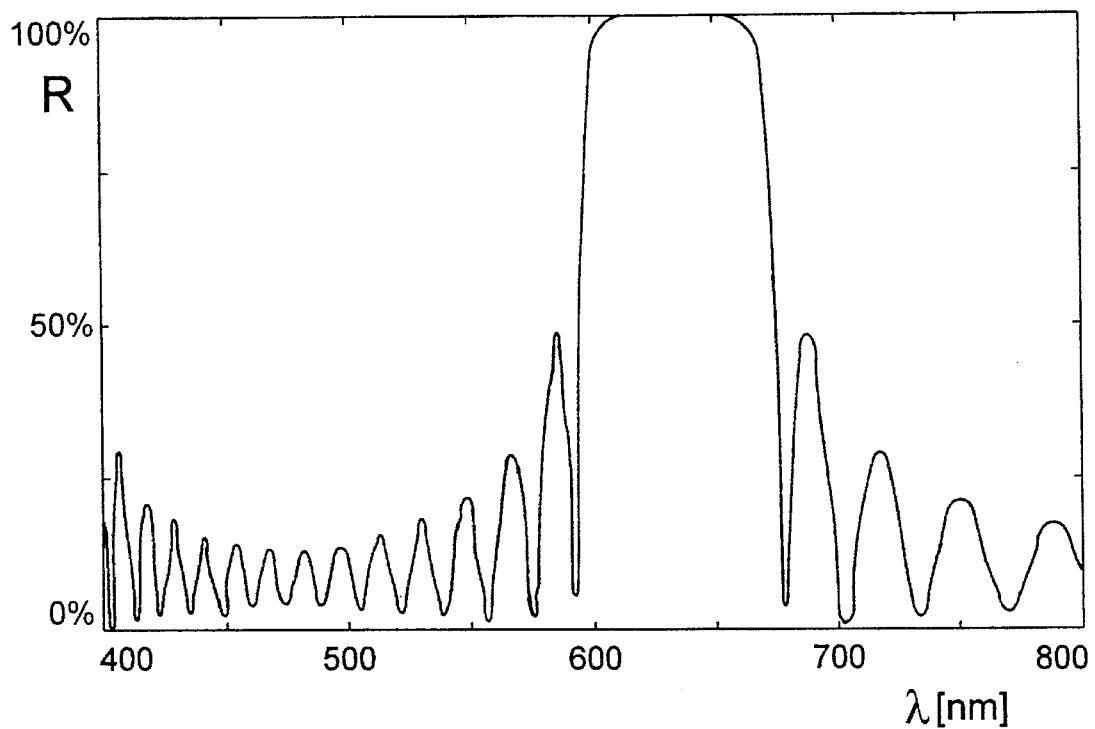
FIG. 1 shows the curve of the reflection factor R.

As illustrated in FIG. 6, an arrangement for protection against electromagnetic radiation of at least one wavelength $\lambda_0$ striking at any angle of incidence comprises a substrate 10 which is transparent at least in the visible spectral range and an absorptive indicator layer realized as an absorbent resonator layer 12 disposed on the substrate for absorbing electromagnetic radiation of wavelength $\lambda_0$ and for indicating absorption of incident radiation energy of wavelength $\lambda_0$ exceeding a threshold energy value $Q_{rad,\ min}$ by undergoing a visible photochemical or photothermal transformation. A plurality of interference layers 14 which are disposed on substrate 10 on a non-incident side of indicator or resonator layer 12 form a backup to the indicator layer for reflecting incident radiation after at least a partial transformation of layer 12 in response to incident radiation energy of wavelength $\lambda_0$ exceeding the threshold energy value $Q_{rad,\ min}$. The interference layers have different refractive indices and are nonabsorbent at least in the spectral range between 450 nm and 750 nm. Absorptive indicator or resonator layer 12 is arranged in sequence with interference layers 14 to provide an optical thin-film resonance absorber system with at least one resonant wavelength $\lambda_r = \lambda_0$. An additional layer 16 is provided on an incident side of absorbent indicator or resonator layer 12. Additional layer 16 is at least virtually non-absorbent at wavelength $\lambda_0$ and is highly sensitive to temperature for purposes of enhancing the indication sensitivity. This temperature-sensitive additional layer 16 is preferably polymeric and produced by dyeing. The polymeric material of layer 16 has, in the visible range, an absorption band which includes wavelength $\lambda_0$ and has a spectral half-width of less than 200 nm.

As discussed hereinabove, absorptive indicator or resonator layer 12 has an indication or conversion sensitivity $R_c$ which is inversely related to a minimum incident radiation energy $Q_{rad,\ min}$ and which increases with decreasing density $\rho$ and decreasing specific heat $c$ of the absorbent layer material, with increasing temperature required for the change in material and with increasing absorption density A/d, where A designates the proportion of radiant energy striking the protective arrangement at wavelength $\lambda_0$ and absorbed in the layer of thickness d. Preferably, density $\rho$ and specific heat $c$ are related as follows:

$$\rho \cdot c \leq 0.6\ cal\ cm^{-3}\ K^{-1} (\cong 2.5 \cdot 10^6\ J\ m^{-3}\ K^{-1}).$$

In Embodiment Examples 1 to 7, absorbent optical media are used as a resonant layer in which the known resonance absorption conditions allow very small resonant layer thicknesses d so that very high absorption densities A/d are achieved. The layer materials in question, including some metals, metalloids and their alloys, metalloid chalcogens, as well as a range of chalcogenides, are distinguished from other chemical elements and compounds in that the real refractive index n and the absorption coefficient k, that is, the real part and the imaginary part of the complex refractive index n–ik, are greater than 1.

In other embodiment examples which are not discussed in the present application, absorbent optical media can be used as a resonant layer in which the resonant layer thickness must be greater than that of the optical media described above due to resonance absorption conditions. The layer materials in question are characterized by absorption coefficients k of less than 1, preferably small in relation to 1. In spite of smaller attainable absorption densities A/d in comparison to the first group of materials, the present materials also have practical importance for the arrangements according to the invention for protection against radiation and indication of radiation because, in some cases, they have a high sensitivity to temperature as a property of the material.

EMBODIMENT EXAMPLE 1

Figure 2:
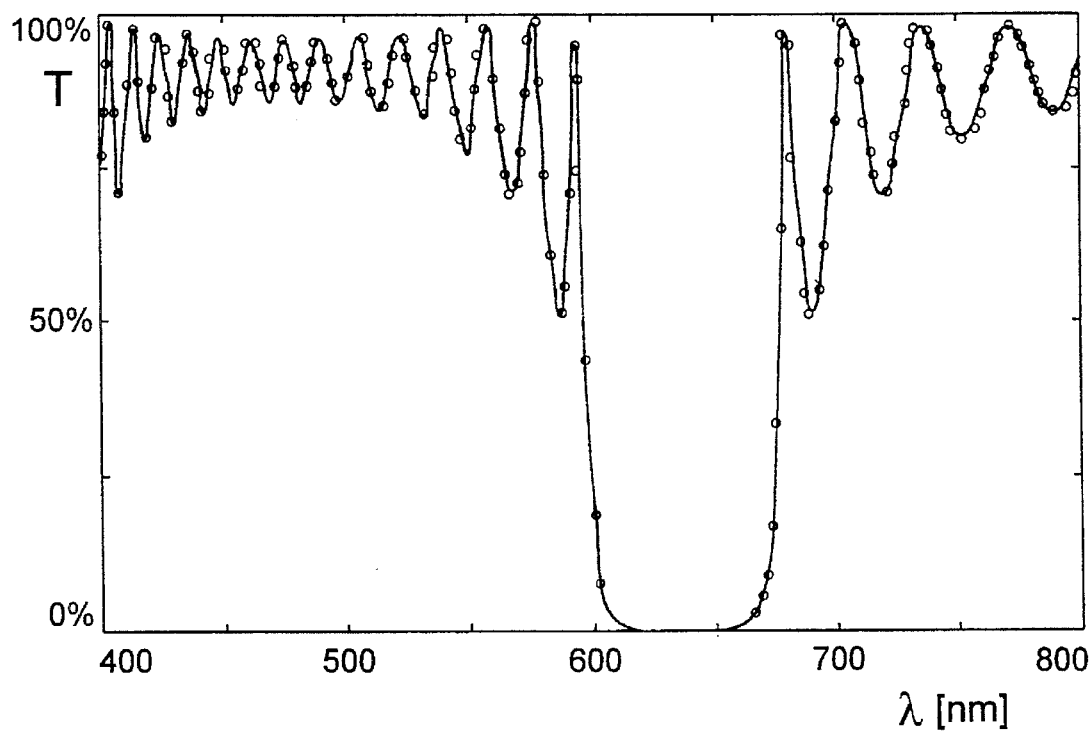
FIG. 2 shows the spectral curve of the transmittance T of the layer system according to a first embodiment example representing the rear resonator wall.

The layer arrangement in this embodiment example is designed to protect against laser radiation of wavelength $\lambda_0 = 633$ nm and to indicate the same. The high reflection of the layer combination representing the rear resonator wall which is required for a high resonator quality in the resonant wavelength is adjusted by means of a sequence of 16 layers with alternating low and high layer refraction indices which are arranged behind the absorbent resonator layer. In the embodiment example this is effected by means of an interference layer system with an optical thickness of $\tfrac{3}{4}\lambda_0$ in each instance, this interference layer system comprising alternating layers of magnesium fluoride and silicon nitride. This interference layer system can also be formed in an advantageous manner purely from oxides, e.g., from $SiO_2$ as low-refractive-index layer substance and $TiO_2$, $ZrO_2$, $Ta_2O_5$, etc. as high-refractive-index layer substance. As shown in FIGS. 1 and 2, the reflection factor R and transmittance T of the interference layer combination in the embodiment example which is applied to glass has a very high reflection in the resonant wavelength, i.e., a very low transmittance, and only a moderate reflection in the visible spectral range outside the narrow spectral interval containing the resonant wavelength, and accordingly has a sufficient transmittance in the rest of the visible spectrum.

Figure 3:
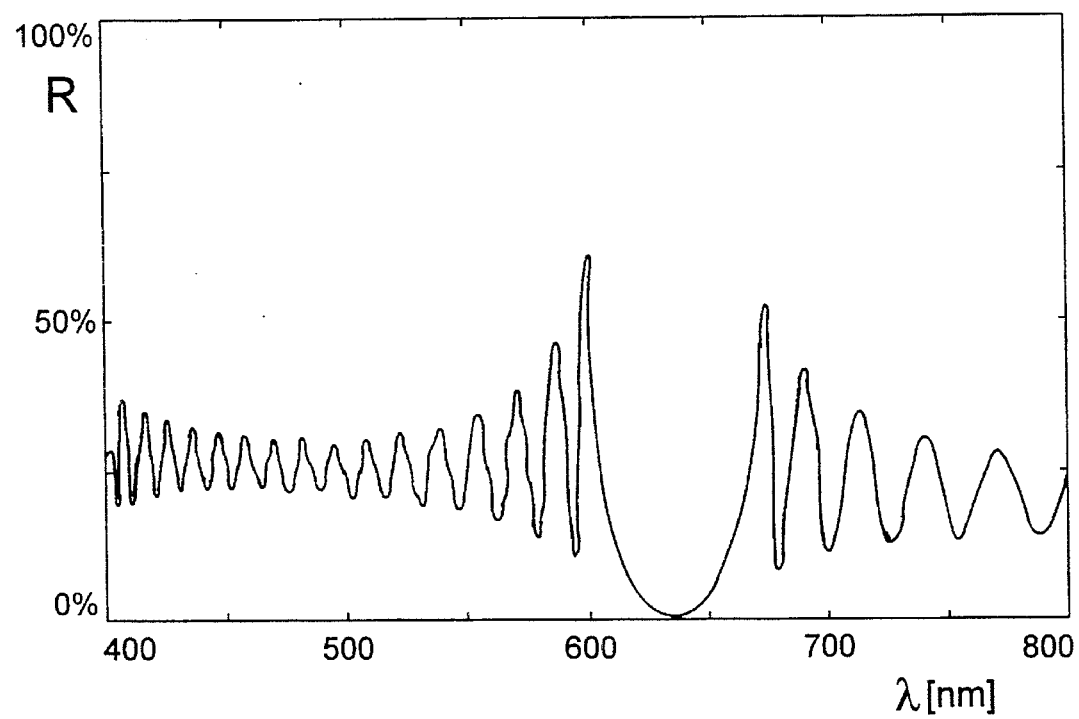
FIG. 3 shows the spectral curve of the reflection factor R.
Figure 4:
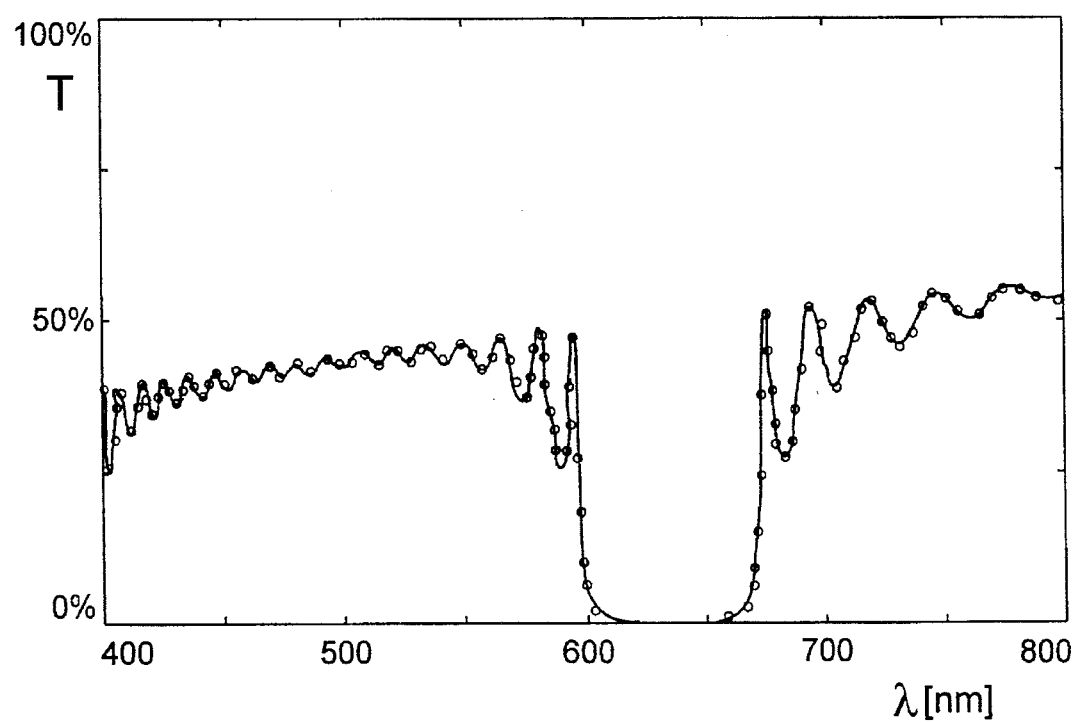
FIG. 4 shows the spectral curve of the transmittance T.

The absorbent resonator layer is made of chromium with the refractive index n–ik≈2.49–i2.3 measured in the mean visible spectral range and has a thickness of 9 nm. With this layer thickness, the reflection disappears relative to air for the thin-film resonance absorber system of the embodiment example. The resonance absorption effect with R≈0, T≈0, A≈100% and with the absorption density A/d≈$\tfrac{1}{9}$ nm$^{-1}$ >0.1 nm$^{-1}$ at the resonance wavelength $\lambda_r=\lambda_0$ relevant for the photothermal or photochemical energy conversion effect is achieved without additional layers arranged in front of the resonator layer. FIGS. 3 to 5 show the spectral curves of reflection factor R, transmittance T and absorption factor A of the thin-film resonance absorber system. At sufficient radiation intensities, the photothermal transformation causes localized destruction of the layer by means of localized fusing of the metal; regions (holes) which are free of substance can occur in the resonant layer at high radiation intensities.

A non-reflecting adaptation of the layer system without front additional layers provides advantages with respect to coating technique insofar as the optimum layer thickness above the reflection minimum can be adjusted during the coating process.

EMBODIMENT EXAMPLE 2

This example differs from the first embodiment example in that the resonator layer thickness is radically reduced at $d\approx3$ nm. However, this requires adapting to the superstratum air so as to be non-reflecting, which is effected by means of a double layer of magnesium fluoride and titanium oxide, each with an optical layer thickness of $\lambda_0/4$, which represents the front resonator wall. At a sufficient radiation intensity, the photothermal transformation produces visible irregularities in material due to localized melting processes in spite of covering the resonator layer with adaptation layers.

EMBODIMENT EXAMPLE 3

In this embodiment example, tellurium is used for the material of the resonant layer. Tellurium also belongs to the group of moderately to highly absorbent resonant layer materials with $n\approx k$ (complex refractive index in the mean visible spectral range: $n-ik\approx4.5-i3$), but is more sensitive to temperature than chromium due to the lower melting point. However, it is also more sensitive to environmental influences. In the present embodiment example, the resonant layer thickness is $d\approx6.5$ nm so as to ensure adaptation to the superstratum air at wavelength $\lambda_0=633$ nm. A protective layer of silicon dioxide with an optical layer thickness of $\lambda_0/2$ which, as is well-known, has no optical effect at wavelength $\lambda_0$ is arranged between the tellurium resonator layer and the air superstratum in order to protect against destruction of the tellurium layer by atmospheric influences, particularly air moisture.

EMBODIMENT EXAMPLE 4

In this embodiment example, tellurium is used as resonant layer with a thickness of $d\approx3$ nm for wavelength $\lambda_0=633$ nm. When the interference layer system which is arranged in the rear as seen in the radiating direction is formed in a manner analogous to Embodiment Example 1, the non-reflecting adaptation is achieved by means of a double layer constructed from a high-refractive-index substance and a low-refractive-index substance, e.g. magnesium fluoride and silicon nitride or silicon oxide and zirconium dioxide or similar combinations.

EMBODIMENT EXAMPLE 5

In this embodiment example, bismuth is used as resonant layer with a thickness of $d\approx9$ nm for wavelength $\lambda_0=488$ nm. At this wavelength, the complex refractive index is $n-ik\approx1.6-i2.7$. When the interference layer system which is arranged in the rear as seen in the radiating direction is formed in a manner analogous to Embodiment Example 1, the non-reflecting adaptation can be achieved e.g. with silicon nitride or a substance with a similar refractive index, where the exact non-reflecting adaptation can be achieved by means of modifying the thickness. This layer which is arranged in front also takes on a protective function.

EMBODIMENT EXAMPLE 6

This example differs from the fifth embodiment example in that the thickness of the bismuth layer is reduced to $d\approx4$ nm. When the interference layer system is arranged behind the resonator layer similar to Embodiment Example 1, but $\lambda_0/4$ layers are selected instead of $3\cdot\lambda_0/4$ layers, a non-reflecting adaptation is achieved by means of a double layer system, e.g. magnesium fluoride and silicon nitride or a combination of substances having similar refractive indices.

EMBODIMENT EXAMPLE 7

In this embodiment example for a wavelength of $\lambda_0\approx800$ nm, antimony tellurium is selected as a resonant layer which is suitable for the reversible indication of harmful radiation due to a reversible photothermal transformation process. When the interference layer system which is arranged in the rear is selected in a manner analogous to Embodiment Example 1, an exact non-reflecting adaptation of the crystalline initial modification of the antimony tellurium to the air superstratum can be achieved with a protective layer (e.g. silicon dioxide) by slightly modifying the thickness.

Embodiment Examples 1 to 7 describe arrangements which can be expanded by an additional layer having high sensitivity to temperature and which are located in direct or indirect contact with the absorbent resonator layer. Such additional layers can be low-melting-point metals, semiconductors or dielectrics which show reversible or irreversible changes at low temperatures. In particularly advantageous embodiment forms, these additional layers are layers of polymers or dye-in polymers which are applied by means of known techniques such as spinning or dipping.

While the foregoing description and drawings represent the preferred embodiments of the present invention, it will be obvious to those skilled in the art that various changes and modifications may be made therein without departing from the true spirit and scope of the present invention.

What is claimed is:

1. An arrangement for protection against electromagnetic radiation of at least one wavelength $\lambda_0$ independently of the incident angle, comprising:

a substrate which is transparent at least in the visible spectral range; and a plurality of interference layers formed on the substrate having different refractive indices;

wherein an additional absorbent resonator layer is arranged in sequence with the interference layers with different refractive indices to provide an optical thin-film resonance absorber system with at least one resonant wavelength $\lambda_r=\lambda_0$;

wherein at least some of the interference layers are arranged on a non-incident side of the absorbent resonator layer as a partial sequence and are nonabsorbent at least in the spectral range between 450 nm and 750 nm, and wherein at a wavelength $\lambda_0$, the absorbent resonator layer is responsive to incident radiation energy exceeding a threshold value $Q_{rad,\ min}$ to undergo a verifiable photo-induced transformation, wherein the material of the absorbent resonator layer has an absorption coefficient k greater than 1 at least at a wavelength $\lambda_0$.

2. The arrangement according to claim 1 wherein the interference layers arranged on the non-incident side of the absorbent resonator layer comprise at least one high refractive index material and at least one low refractive index material, and constitute an optical stack of alternately high and low refractive index layers.

3. The arrangement according to claim 2 wherein the optical thickness $n_s \cdot d_s$ of each interference layer arranged on the non-incident side of the absorbent resonator layer is $n_s \cdot d_s = (m+1))\lambda_0/4$, where $n_s$ is the refractive index of the individual layer, $d_s$ is the geometric thickness of the individual layer and m equals an integer, and wherein the interference layers arranged on the non-incident side of the absorbent resonator layer have a reflection factor relative to air of greater than 99% in a spectral interval containing wavelength $\lambda_0$ within the wavelength range of $0.9 \cdot \lambda_0$ to $1.1 \cdot \lambda_0$ and a reflection factor relative to air of less than 50% in a spectral interval in the visible spectral range outside the wavelength range of $0.9 \cdot \lambda_0$ to $1.1 \cdot \lambda_0$, so that the partial sequence of interference layers arranged on the non-incident side of the absorbent resonator layer has a pseudo-refractive index of $\leq 0.1$ at a wavelength $\lambda_0$ when the first incident layer in the partial sequence has a low refractive index.

4. Arrangement according to claim 2 wherein the optical thickness $n_s \cdot d_s$ of each interference layer arranged on the non-incident side of the absorbent resonator layer is $n_s \cdot d_s = (m+1)\lambda_0/4$, where $n_s$ is the refractive index of the individual layer, $d_s$ is the geometric thickness of the individual layer and m equals an integer, and wherein the interference layers arranged on the non-incident side of the absorbent resonator layer have a reflection factor relative to air of greater than 99% in a spectral interval containing wavelength $\lambda_0$ within the wavelength range of $0.9 \cdot \lambda_0$ to $1.1 \cdot \lambda_0$ and a reflection factor relative to air of less than 50% in a spectral interval in the visible spectral range outside the wavelength range of $0.9 \cdot \lambda_0$ to $1.1 \cdot \lambda_0$, so that the partial sequence of interference layers arranged on the non-incident side of the absorbent resonator layer has a pseudo-refractive index of $\geq 10$ at a wavelength $\lambda_0$ when the first incident layer in the partial sequence has a high refractive index.

5. The arrangement according to claim 1, wherein the material of the absorbent resonator layer has a density $\rho$ and a specific heat c whose product is $$\rho \cdot c \leq 0.6 \; cal \; cm^{-3} \; K^{-1} (\cong 2.5 \cdot 10^6 \; J \; m^{-3} K^{-1}).$$

6. The arrangement according to claim 1, wherein an additional layer which is at least substantially non-absorbent at the wavelength $\lambda_0$ of hazardous radiation and which is highly sensitive to temperature is provided in proximity to the absorbent resonator layer in order to increase the indication sensitivity.

7. The arrangement according to claim 6, wherein the additional layer which is highly sensitive to temperature is arranged immediately in front of the absorbent resonator layer on the incident side thereof.

8. The arrangement according to claim 6, wherein the additional layer which is highly sensitive to temperature is a polymer.

9. The arrangement according to claim 6, wherein the additional layer which is highly sensitive to temperature has, in the visible spectral range, an absorption band which excludes the wavelength $\lambda_0$ and has a spectral half-width value of less than 200 nm.

10. The arrangement according to claim 6, wherein the absorption of the additional layer which is highly sensitive to temperature results from dyeing.

11. A method for protecting eyes from damaging radiation of wavelength $\lambda_0$, comprising:

providing a protective device including an absorbent resonator layer on an optically transparent substrate also carrying a plurality of interference layers having different refractive indices, the plurality of interference layers being nonabsorbent at least in the spectral range between 450 nm and 750 nm, said interference layers being disposed on a non-incident side of the absorbent resonator layer; said absorbent resonator layer being arranged in sequence with the interference layers with different refractive indices to provide an optical thin-film resonance absorber system with at least one resonant wavelength $\lambda_r = \lambda_0$;

disposing said device between a source of radiation of wavelength $\lambda_0$ and an eye of a user;

operating said source to emit radiation of wavelength $\lambda_0$;

absorbing emitted radiation of wavelength $\lambda_0$ in said absorbent resonator layer;

reflecting from said plurality of interference layers any radiation of wavelength $\lambda_0$ which penetrates beyond said absorbent resonator layer; and in the event that radiation incident on said absorbent resonator layer exceeds a threshold energy value $Q_{rad, min}$, transforming said absorbent resonator layer to provide a verifiable indication that incident radiation of wavelength $\lambda_0$ has exceeded the threshold energy value $Q_{rad, min}$.

12. Arrangement for protection against electromagnetic radiation of at least one wavelength $\lambda_0$ independently of the incident angle, comprising:

a substrate which is transparent at least in the visible spectral range;

absorptive indicator means disposed on said substrate for absorbing electromagnetic radiation of wavelength $\lambda_0$ and for indicating absorption of incident radiation energy of wavelength $\lambda_0$ exceeding a threshold energy value $Q_{rad, min}$ by undergoing a visible transformation; and backup means disposed on said substrate on a non-incident side of said absorptive indicator means for reflecting incident radiation after at least a partial transformation of said absorptive indicator means in response to incident radiation energy of wavelength $\lambda_0$ exceeding said threshold energy value $Q_{rad, min}$, said backup means including a plurality of interference layers having different refractive indices, said plurality of interference layers being nonabsorbent at least in the spectral range between 450 nm and 750 nm, said absorptive indicator means including an absorbent resonator layer arranged in sequence with the interference layers to provide an optical thin-film resonance absorber system with at least one resonant wavelength $\lambda_r = \lambda_0$.

13. Arrangement according to claim 12 wherein the interference layers, which are arranged on the non-incident side of the absorbent resonator layer, comprise at least one high refractive index material and at least one low refractive index material, and constitute an optical stack of alternately high and low refractive index layers.

14. Arrangement according to claim 13 wherein the optical thickness $n_s \cdot d_s$ of each of said interference layers is $n_s \cdot d_s = (m+1)\lambda_0/4$, where $n_s$ is the refractive index of the individual layer, $d_s$ is the geometric thickness of the individual layer and m equals an integer, and wherein said interference layers have a reflection factor relative to air of greater than 99% in a spectral interval containing wavelength $\lambda_0$ within the wavelength range of $0.9 \cdot \lambda_0$ to $1.1 \cdot \lambda_0$ and a reflection factor relative to air of less than 50% in a spectral interval in the visible spectral range outside the wavelength range of $0.9 \cdot \lambda_0$ to $1.1 \cdot \lambda_0$, so that the partial sequence of interference layers arranged on the non-incident side of the absorbent resonator layer has a pseudo-refractive index of $\leq 0.1$ at a wavelength $\lambda_0$ when the partial sequence begins with a layer with a low refractive index and is $\geq 10$ when the first incident layer in the partial sequence has a high refractive index.

15. An arrangement for protection against electromagnetic radiation of at least one wavelength $\lambda_0$ independently of the incident angle, having a substrate which is transparent at least in the visible spectral range and a plurality of interference layers formed on the substrate having different refractive indices, wherein an additional absorbent resonator layer is arranged in sequence with the interference layers with different refractive indices to provide an optical thin-film resonance absorber system with at least one resonant wavelength $\lambda_r = \lambda_0$, wherein the interference layers arranged on a non-incident side of the absorbent resonator layer are nonabsorbent at least in the spectral range between 450 nm and 750 nm, and wherein at a wavelength $\lambda_0$, the absorbent resonator layer is responsive to incident radiation energy exceeding a threshold value $Q_{rad, min}$ to undergo a verifiable photo-induced transformation;

wherein at least some of the interference layers are arranged on the non-incident side of the absorbent resonator layer as a partial sequence and comprise at least one high refractive index material and at least one low refractive index material arranged as an optical stack of alternately high and low refractive index layers; and wherein the optical thickness $n_s \cdot d_s$ of each interference layer arranged on the non-incident side of the absorbent resonator layer is $n_s \cdot d_s = (m+1)\lambda_0/4$, where $n_s$ is the refractive index of the individual layer, $d_s$ is the geometric thickness of the individual layer and m equals an integer, and wherein the interference layers arranged on the non-incident side of the absorbent resonator layer have a reflection factor relative to air of greater than 99% in a spectral interval containing wavelength $\lambda_0$ within the wavelength range of $0.9 \cdot \lambda_0$ to $1.1 \cdot \lambda_0$ and a reflection factor relative to air of less than 50% in a spectral interval in the visible spectral range outside the wavelength range of $0.9 \cdot \lambda_0$ to $1.1 \cdot \lambda_0$, so that the partial sequence of interference layers arranged on the non-incident side of the absorbent resonator layer has a pseudo-refractive index of $\leq 0.1$ at a wavelength $\lambda_0$ when the first incident layer in the partial sequence has a low refractive index.

16. An arrangement for protection against electromagnetic radiation of at least one wavelength $\lambda_0$ independently of the incident angle, having a substrate which is transparent at least in the visible spectral range and a plurality of interference layers formed on the substrate having different refractive indices, wherein an additional absorbent resonator layer is arranged in sequence with the interference layers with different refractive indices to provide an optical thin-film resonance absorber system with at least one resonant wavelength $\lambda_r = \lambda_0$, wherein at least some of the interference layers are arranged on a non-incident side of the absorbent resonator layer to form a partial sequence and are nonabsorbent at least in the spectral range between 450 nm and 750 nm, and wherein at a wavelength $\lambda_0$, the absorbent resonator layer is responsive to incident radiation energy exceeding a threshold value $Q_{rad, min}$ to undergo a verifiable photo-induced transformation;

wherein the interference layers arranged on the non-incident side of the absorbent resonator layer comprise at least one high refractive index material and at least one low refractive index material arranged as an optical stack of alternately high and low refractive index layers; and wherein the optical thickness $n_s \cdot d_s$ of each interference layer arranged on the non-incident side of the absorbent resonator layer is $n_s \cdot d_s = (m+1)\lambda_0/4$, where $n_s$ is the refractive index of the individual layer, $d_s$ is the geometric thickness of the individual layer and m equals an integer, and wherein the interference layers arranged on the non-incident side of the absorbent resonator layer have a reflection factor relative to air greater than 99% in a spectral interval containing wavelength $\lambda_0$ within the wavelength range of $0.9 \cdot \lambda_0$ to $1.1 \cdot \lambda_0$ and a reflection factor relative to air less than 50% in a spectral interval in the visible spectral range outside the wavelength range of $0.9 \cdot \lambda_0$ to $1.1 \cdot \lambda_0$, so that the partial sequence of optical layers arranged on the non-incident side of the absorbent resonator layer has a pseudo-refractive index of $\geq 10$ at a wavelength $\lambda_0$ when the first incident layer in the partial sequence has a high refractive index.

* * * * *